US012741037B2

(12) United States Patent
Su et al.

(10) Patent No.: US 12,741,037 B2
(45) Date of Patent: Sep. 22, 2026

(54) LIVER-TARGETED FLUORESCENCE/PHOTOACOUSTIC DUAL-MODAL PROBE FOR EARLY DETECTING DRUG-INDUCED HEPATIC INFLAMMATION AND AUTOIMMUNE HEPATITIS

(71) Applicant: BEIJING UNIVERSITY OF TECHNOLOGY, Beijing (CN)

(72) Inventors: Dongdong Su, Beijing (CN); Yong Zhang, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 922 days.

(21) Appl. No.: 18/092,300

(22) Filed: Dec. 31, 2022

(65) Prior Publication Data

US 2024/0165272 A1 May 23, 2024

(30) Foreign Application Priority Data

Oct. 31, 2022 (CN) ........................ 202211349415.0

(51) Int. Cl.
*A61K 49/00* (2006.01)
*A61B 5/00* (2006.01)
*A61B 5/1455* (2006.01)

(52) U.S. Cl.
CPC ........ *A61K 49/0002* (2013.01); *A61B 5/0095* (2013.01); *A61B 5/14556* (2013.01)

(58) Field of Classification Search
CPC ............ A61K 49/0002; A61K 49/0021; A61K 49/0052; A61K 49/221; A61B 5/0095; A61B 5/14556; A61B 5/4244; A61B 5/0071
See application file for complete search history.

*Primary Examiner* — Robert S Cabral
(74) *Attorney, Agent, or Firm* — J.C. PATENTS

(57) ABSTRACT

A liver-targeted fluorescence/photoacoustic dual-modal probe for the early detection of drug-induced hepatic inflammation and autoimmune hepatitis is disclosed. The chemical makeup of the probe hCy-Tf-CA is shown in Equation 1. The fluorescence and photoacoustic signal of probe-only solution is very weak, the dual-modal signal was significantly increased after selectively reacting with $O_2^{\cdot-}$. The probe has the advantages of early preparation, live-targeting ability, high selectivity and sensitivity and dual-modal imaging. The probe can in situ visualization of $O_2^{\cdot-}$ in early hepatic inflammation with fluorescent/photoacoustic dual-modal imaging, providing a potential strategy in biomedical field with broad application prospects.

2 Claims, 11 Drawing Sheets

LIVER-TARGETED FLUORESCENCE/PHOTOACOUSTIC DUAL-MODAL PROBE FOR EARLY DETECTING DRUG-INDUCED HEPATIC INFLAMMATION AND AUTOIMMUNE HEPATITIS

CROSS REFERENCE TO RELATED APPLICATION

This application claims priority benefit of Chinese Patent Application No. 202211349415.0, filed on Oct. 31, 2022, which is hereby incorporated by reference in its entirety.

TECHNICAL FIELD

In general, the invention relates to in vivo visualization of the concentration and distribution of superoxide ($O_2^{\cdot-}$) with a small molecular fluorescent/photoacoustic dual-modal probe, and in particular to a hemi-cyanine fluorophore based probe for accurately detecting endogenous $O_2^{\cdot-}$, which belongs to the field of fluorescence/photoacoustic dual-modal bioimaging.

BACKGROUND

Liver is the main metabolic organ of the human body. The incidence of hepatic inflammation is gradually increasing, and the higher the risk of exposure to adverse conditions such as overdose of drugs, intemperance, allergies, viruses and intestinal microbial metabolites, the greater the incidence of hepatic inflammation, with varying degrees of hypohepatia. At present, the incidence of hepatic inflammation is gradually increasing. If left untreated, hepatic inflammation may continue to progress and eventually develop into severe complications. Therefore, accurate diagnosis of early hepatic inflammation may provide the opportunity for timely intervention to reduce the risk of disease progression. Currently, the clinical diagnosis of hepatic inflammation depends on liver function tests, which mainly check the abnormal levels of alanine aminotransferase (ALT) and aspartate aminotransferase (AST) in serum. Unfortunately, hepatic inflammation is easy to miss in its early stages because the symptoms are atypical and the abnormal blood markers detected are associated with many diseases throughout the body. Therefore, the early clinical detection of hepatic inflammation is a challenge, and there is an urgent need to develop new strategies capable of detection and accurate pathological analysis of early hepatic inflammation in real time.

Intracellular reactive oxygen species (ROS), as the key participants in oxidative stress, fluctuate dynamically with pathological processes. It is worth noting that $O_2^{\cdot-}$ is the primary ROS in the event of hepatocellular oxidative stress, and is the main source of other ROS and reactive nitrogen species (RNS). Therefore, $O_2^{\cdot-}$ can be considered as a pivotal early parameter of liver dysfunction, which in turn is involved in hepatic inflammation and ultimately hepatocyte necrosis. Therefore, it can be used as a key analyte for the early diagnosis of hepatic inflammation. Due to the high reactivity and short half-life of $O_2^{\cdot-}$, real-time detection of $O_2^{\cdot-}$ in vivo is difficult. Therefore, it is necessary to develop alternative methods to monitor the fluctuation of hepatic $O_2^{\cdot-}$ in situ in order to promote the early diagnosis of hepatic inflammation.

NIR fluorescence probes are a promising diagnostic tool with strong imaging sensitivity for non-invasive detection of analytes of interest in vivo. In recent years, more attention has been paid to the development of fluorescent probes with high sensitivity and specificity for early markers of hepatic inflammation, which are expected to be used for in situ detection of hepatic inflammation. However, the tissue penetration ability of single NIR imaging is not enough to realize high spatial resolution visualization of deep tissue pathology information. Notably, photoacoustic (PA) imaging combines the imageological superiorities of fluorescence and ultrasound imaging to further facilitate real-time monitoring of internal physiological and pathological conditions in deep tissues. Because the imaging mechanism of NIRF imaging is similar to that of PA imaging, it makes sense to integrate the two imaging modalities with a probe. Through the two-in-one strategy, NIRF/PA dual-modal imaging possess both high sensitivity of fluorescence imaging and high penetration depth and high spatial resolution of PA, and can capture more comprehensive pathological information, becoming a promising strategy for precision medicine.

Although dual-modal probes provide novel strategies for precision medicine, small molecule dual-modal probes for in vivo bioimaging still face several challenges, such as low signal-to-background ratio (SBR) caused by their repaid clearance and unpredictable biodistribution in the lesion area. High dose probes can enhance SBR to some extent, but may cause potential metabolic stress. Enhancing active targeting capability is one of the most common strategies to improve the imaging performance of molecular probes. For example, based on the abundant galactose receptor protein on the surface of hepatocytes, galactose decoration can effectively promote probe accumulation in the liver. Therefore, in order to accurately diagnose liver diseases, more alternative targets that can improve liver targeting and facilitate probe design need to be developed. Cholic acid (CA) is a high affinity substrate for several hepatocyte-surface receptor and can be efficiently internalized into the liver, which can be used as a targeting group to achieve efficient enrichment of probes in the liver.

In order to overcome the poor accuracy of liver inflammation detection, liver-targeted fluorescence/photoacoustic dual-modal probes for the specific response to early markers of liver inflammation should be developed. We suppose that the active targeting strategy combined with the activatable dual-modal imaging synergistically improve in situ imaging performance and allow for early and accurate diagnosis of hepatic inflammation.

SUMMARY

The invention provides a liver-targeted fluorescent/photoacoustic dual-modal imaging probe (hCy-Tf-CA) for real-time imaging of in situ hepatic inflammation, and its preparation method. The probe has the advantages of liver targeting ability and fluorescence/photoacoustic dual-modal imaging. With these advantages, the probe can in situ visualize $O_2^{\cdot-}$ in early hepatic inflammation with high selectivity and sensitivity, providing an effective method to facilitate precise imaging of hepatic inflammation.

In order to solve the above technical problems, the technical solutions are as follows:

The invention provides a liver-targeted fluorescent/photoacoustic dual-modal probe for real-time imaging of in situ hepatic inflammation, and the chemical makeup is as follows:

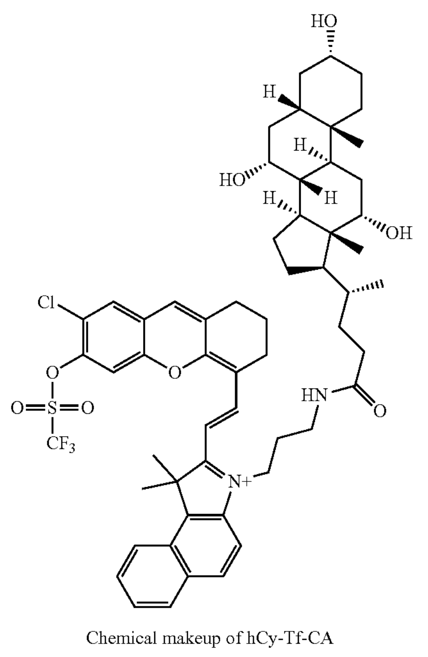

Chemical makeup of hCy-Tf-CA

The invention provides a method for preparing a liver-targeted fluorescent/photoacoustic bimodal probe. The detailed synthesis is as follow:

Trifluoromethanesulfonic anhydride was dropwise added to a mixture of hCy-NHBoc and triethylamine in anhydrous $CH_2Cl_2$ in an ice bath under nitrogen atmosphere. When the reaction is complete, it was quenched by ice water. The organic layer was carefully separated and directly purified by column chromatography to afford the intermediate hCy-Tf-NHBoc as a purple solid. Subsequently, the intermediate hCy-Tf-NHBoc was added anhydrous $CH_2Cl_2$ containing 25% trifluoroacetic acid. After the reaction is complete, the reaction solution was evaporated under reduced pressure and the resulting residue was washed with diethyl ether to afford crude intermediate hCy-Tf-$NH_2$. Then hCy-Tf-$NH_2$, cholic acid, HBTU, HOBT and DIPEA were dissolved in DMF. After the reaction is complete, the solvent was removed by excess petroleum ether, and the resulting residue was purified by column chromatography to afford the liver-targeted fluorescence/photoacoustic dual-modal probe hCy-Tf-CA as a purple solid.

The synthesis route of hCy-Tf-CA is as follow:

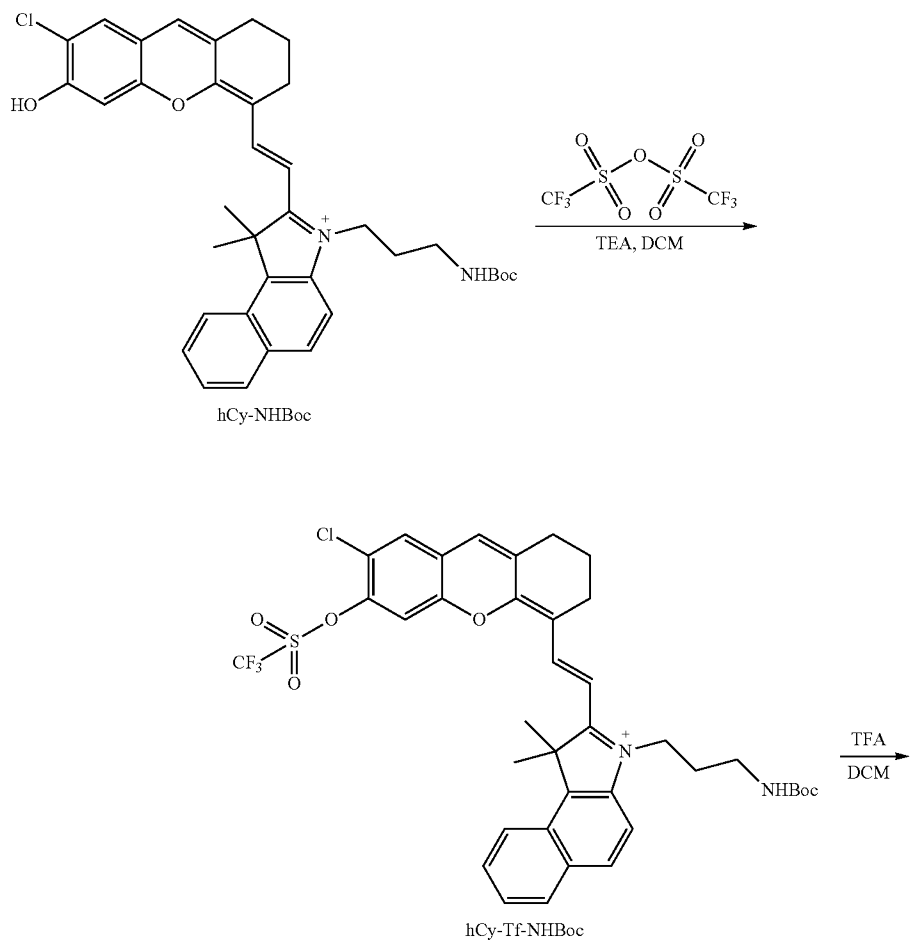

hCy-NHBoc hCy-Tf-NHBoc

-continued

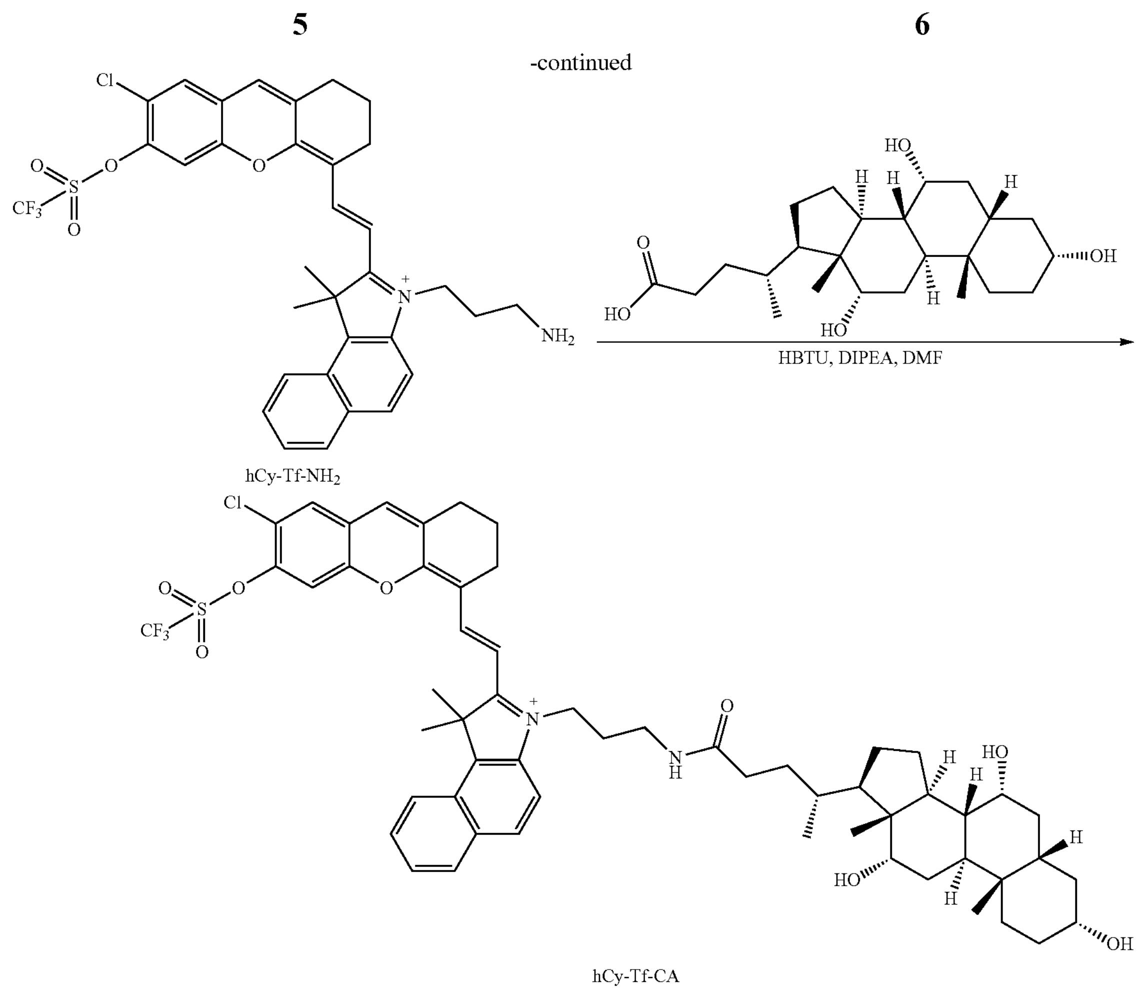

hCy-Tf-$NH_2$ hCy-Tf-CA

In addition, the invention aims to provide a fluorescent probe for the detection of endogenic $O_2^{\cdot-}$ in cells. More importantly, the invention aims to in situ visualization of pathological $O_2^{\cdot-}$ in early hepatic inflammation by fluorescence/photoacoustic dual-modal imaging, providing an effective method to facilitate precise imaging of hepatic inflammation.

The invention has the following advantages:

The liver-targeted fluorescence/photoacoustic dual-modal probe provided by the invention can specifically react with $O_2^{\cdot-}$, and its fluorescence intensity is significantly increased by 17 times. At the same time the probe shows good chemical stability and biocompatibility.

The probe of the invention has high selectivity and anti-interference. It barely responds to various potential interferents ($Na^+$, $K^+$, $Ca^{2+}$, $Mg^{2+}$, $Zn^{2+}$, $Cu^{2+}$, $HS^-$, HClO, $H_2O_2$, ·OH, $ONOO^-$, glucose, glutathione, cysteine, vitamin C, nitroreductase, alkaline phosphatase, β-galactosidase and leucine aminopeptidase), just shows significant response to $O_2^{\cdot-}$ with rapidly increased fluorescence.

The probe of the invention shows good biocompatibility, and can visual monitor $O_2^{\cdot-}$ fluctuation in cells under different drug stimulation.

By fluorescence/photoacoustic dual-mode imaging, the invention provides a reliable method for in situ real-time monitoring hepatic $O_2^{\cdot-}$ and early hepatic inflammation in a noninvasive manner, which shows a broad application prospect in bioanalysis field.

LEGEND

DETAILED DESCRIPTION OF THE PREFERRED EMBODIMENTS

The present disclosure will be further described below with the preferred embodiment, but the present invention is not limited to the following examples.

Trifluoromethanesulfonic anhydride was dropwise added to a mixture of hCy-NHBoc and triethylamine in anhydrous dichloromethane in an ice bath under nitrogen atmosphere. After stirring for 5 minutes, it was quenched by ice water. The organic layer was carefully separated and directly purified by column chromatography to afford the intermediate hCy-Tf-NHBoc as a purple solid. Subsequently, the intermediate hCy-Tf-NHBoc was added anhydrous dichloromethane containing 25% trifluoroacetic acid. After stirring for 5 minutes, the reaction solution was evaporated under reduced pressure and the resulting residue was washed with diethyl ether to afford crude intermediate hCy-Tf-$NH_2$. Then hCy-Tf-$NH_2$, cholic acid, o-Benzotriazol-1-yl-N,N,N',N'-tetramethyluronium hexafluorophosphate, 1-Hydroxybenzotriazole and N,N-Diisopropylethylamine were dissolved in N,N-Dimethylformamide. After the reaction is complete, the solvent was removed by excess petroleum ether, and the resulting residue was purified by column chromatography to afford the liver-targeted fluorescence/photoacoustic dual-modal probe hCy-Tf-CA as a purple solid.

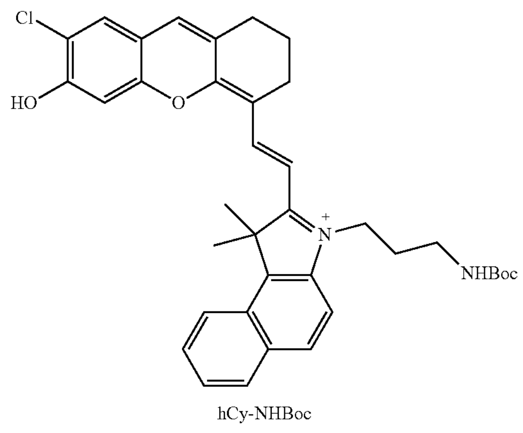

hCy-NHBoc

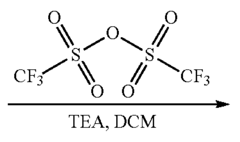

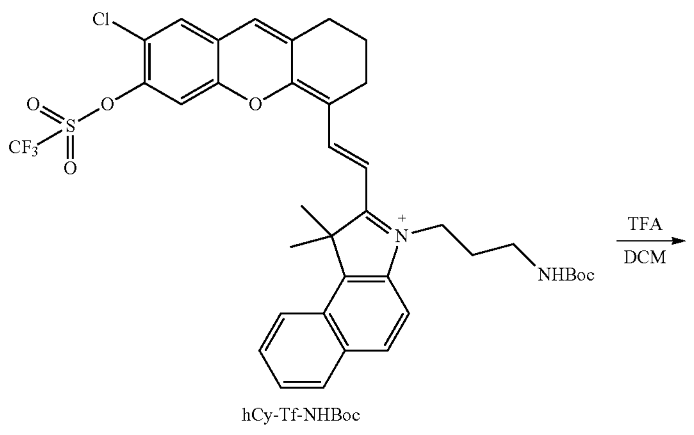

hCy-Tf-NHBoc

-continued

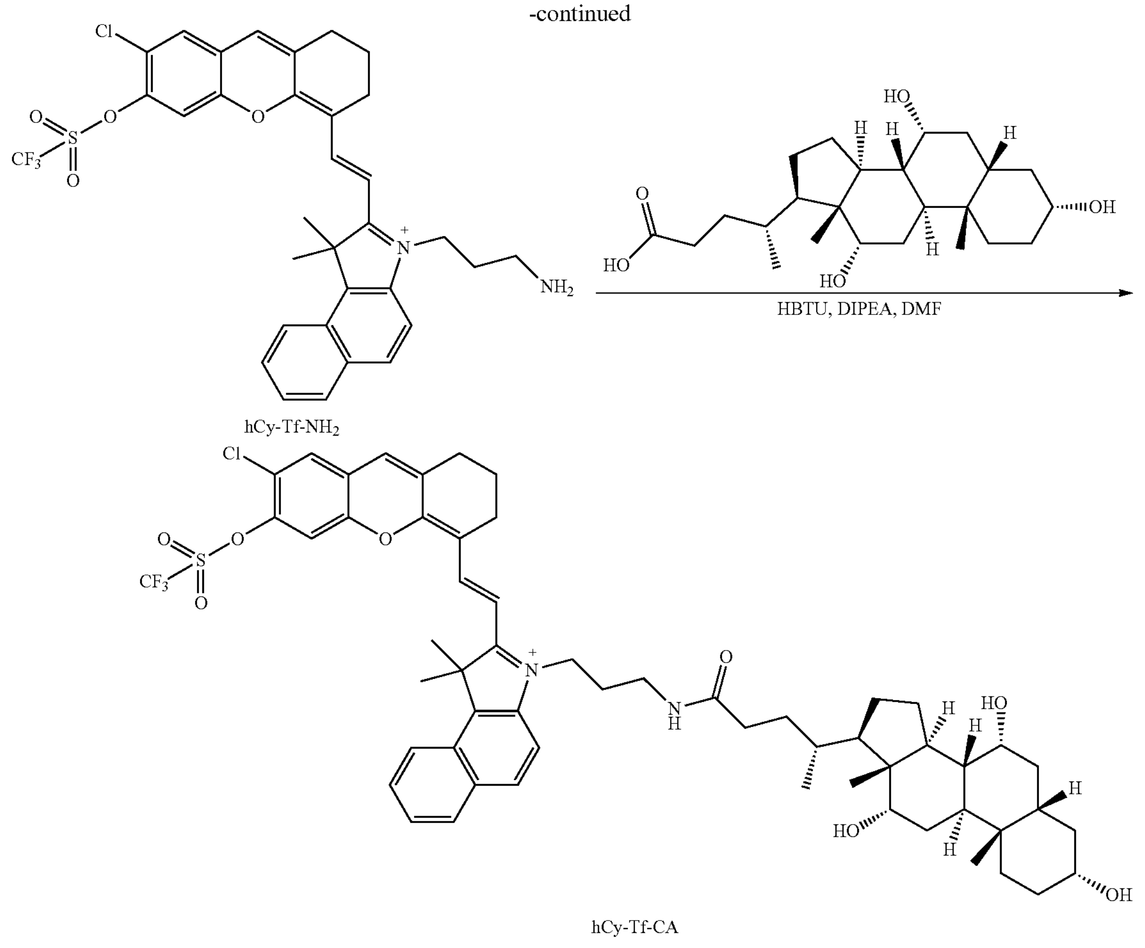

hCy-Tf-$NH_2$ hCy-Tf-CA

The molar ratio of hCy-NHBoc, trifluoromethanesulfonic anhydride and triethylamine was 1:1.2:1.2.

The volume ratio of methanol to dichloromethane was 1:50 in the first silica gel column chromatography.

The molar ratio of hCy-Tf-NHBoc to trifluoroacetic acid was 1:536.

The molar ratio of hCy-Tf-$NH_2$, cholic acid, o-Benzotriazol-1-yl-N,N,N',N'-tetramethyluronium hexafluorophosphate, 1-Hydroxybenzotriazole and N,N-Diisopropylethylamine is 1:1.2:1.2:1.2:2.

The volume ratio of methanol to dichloromethane was 1:10 in the second silica gel column chromatography.

Nuclear magnetic resonance CH NMR and $^{13}C$ NMR) confirmed the structures of the intermediate hCy-Tf-NHBoc and the final probe hCy-Tf-CA (FIG. 16-19), which prove the successful synthesis of the liver-targeted fluorescent/photoacoustic dual-modal probe hCy-Tf-CA.

Embodiment 2

Figure 1:
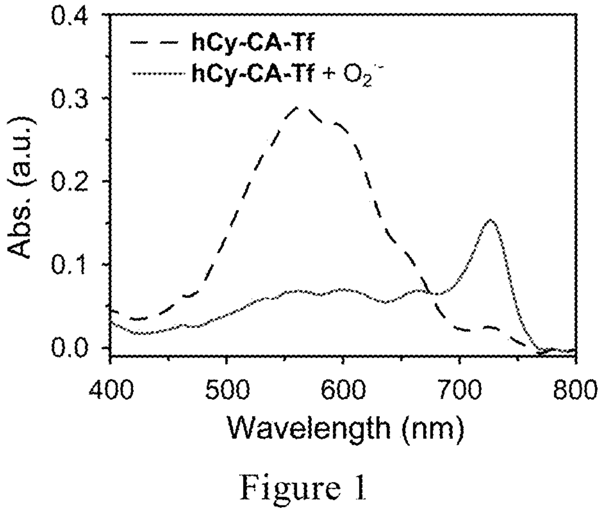
FIG. 1 shows absorption spectra of the $O_2^{\cdot-}$-responsive liver-targeted fluorescence/photoacoustic dual-modal probe hCy-Tf-CA (10 μM) before and after reacting with $O_2^{\cdot-}$ (100 μM). Solvent: ethanol-phosphate buffer solution (ethanol/PBS=1/1, v/v, pH=7.4).

Absorption Spectra of hCy-Tf-CA Before and After the Reaction With $O_2^{\cdot -}$ 10 μL of probe stock solution (1 mM) was added to 1 mL of ethanol-phosphate buffer solution (ethanol/PBS=1/1, v/v, pH=7.4). To characterize the responsiveness of hCy-Tf-CA, 40 μL $O_2^{\cdot -}$ stock solution (2.5 mM) was added to above solution. FIG. 1 shows the absorption spectra of hCy-Tf-CA (10 μM) before and after reacting with $O_2^{\cdot -}$ (100 μM) for 10 min. hCy-Tf-CA shows broad absorption (500-650 nm) with a peak at around 550 nm. After incubation with $O_2^{\cdot -}$, the absorption peak of hCy-Tf-CA at 550 nm decreased significantly, accompanied by the appearance of a new absorption peak at 725 nm, proving the fast response of hCy-Tf-CA to $O_2^{\cdot -}$.

Embodiment 3

Figure 2:
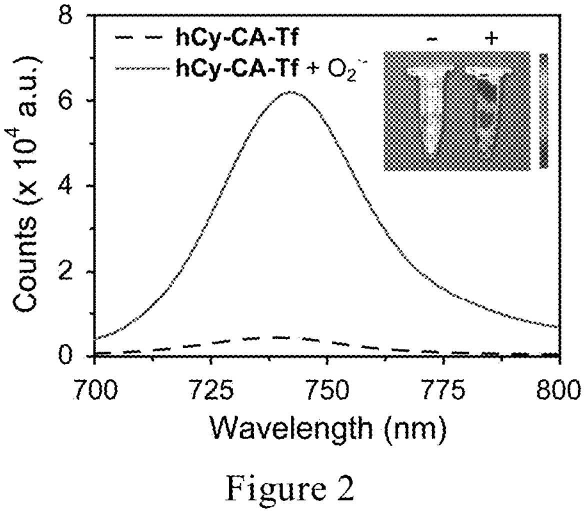
FIG. 2 shows fluorescence spectra of hCy-Tf-CA (10 μM) before and after reacting with $O_2^{\cdot-}$ (100 μM). $\lambda_{ex}$=680 nm

Fluorescence Spectra of hCy-Tf-CA Before and After the Reaction With $O_2^{\cdot -}$ The reaction system was prepared under the same experimental conditions. FIG. 2 shows the fluorescence spectra of hCy-Tf-CA (10 μM) before and after reacting with $O_2^{\cdot -}$ (100 μM) for 10 min. FIG. 2 shows that hCy-Tf-CA is almost non-fluorescent at 725 nm when irradiated by 680 nm excitation light. After incubation with $O_2^{\cdot -}$, fluorescence spectrum of hCy-Tf-CA is significantly increased, and the fluorescence intensity at 730 nm increased 17-fold compared with probe alone. Meanwhile, the NIRF images of hCy-Tf-CA recorded by a IVIS imaging system ($\lambda_{ex}$=675 nm, $\lambda_{em}$=760 nm) show little fluorescence of the probe itself, and the fluorescence signal was significantly enhanced after $O_2^{\cdot -}$ treatment. That is due to the nucleophilic $O_2^{\cdot -}$ cleavage of trifluoromethonium sulfonate, which restored the strong electron-donating phenol and it-conjugation on the fluorophore. The results show that hCy-Tf-CA can respond to $O_2^{\cdot -}$ with high sensitivity and fast speed. The probe hCy-Tf-CA is an enhanced fluorescence probe.

Embodiment 4

Figure 3:
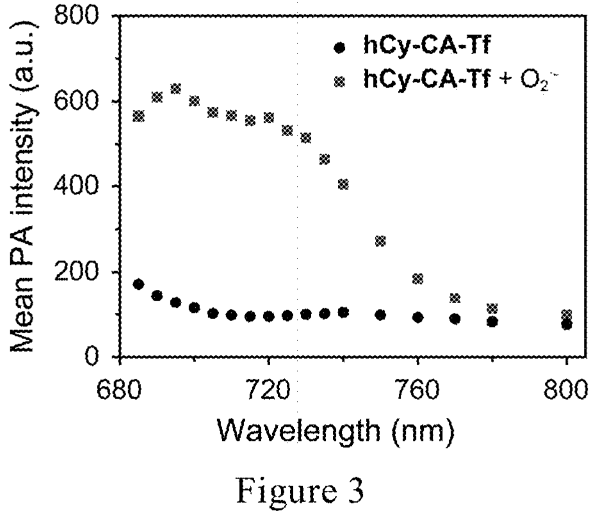
FIG. 3 shows photoacoustic spectra of hCy-Tf-CA (10 μM) before and after reacting with $O_2^{\cdot-}$ (100 μM).

Photoacoustic Spectra of hCy-Tf-CA Before and After the Reaction With $O_2^{\cdot-}$ The reaction system was prepared under the same experimental conditions. FIG. 3 shows the photoacoustic spectra of hCy-Tf-CA (10 μM) before and after reacting with $O_2^{\cdot-}$ (100 μM) for 10 min. The photoacoustic signal of hCy-Tf-CA only at 710 nm is very weak (FIG. 3). As expected, the photoacoustic signal of hCy-Tf-CA showed a 7-fold enhancement at 710 nm after treated with $O_2^{\cdot-}$. Above results show that hCy-Tf-CA can respond to $O_2^{\cdot-}$ sensitively and the probe hCy-Tf-CA is an enhanced photoacoustic probe.

Embodiment 5

Fluorescence Response of hCy-Tf-CA to Different Concentration of $O_2^{\cdot-}$

Figure 4:
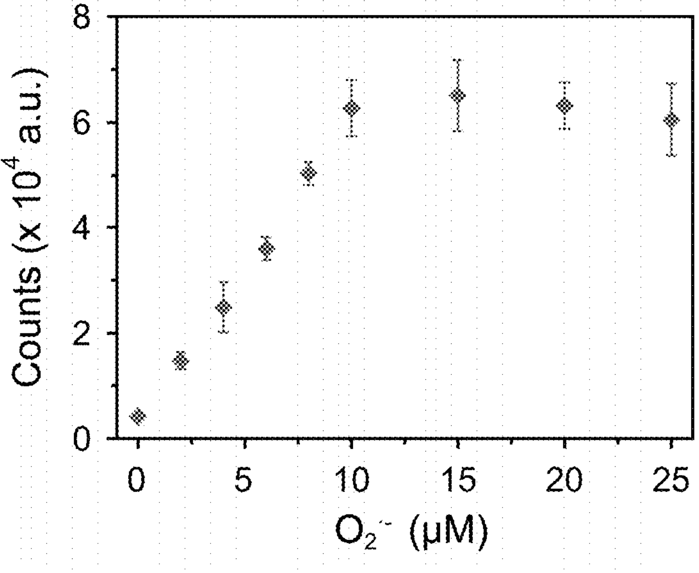
FIG. 4 shows fluorescence intensity of hCy-Tf-CA (10 μM) at 730 nm after 10 min incubation with different concentration $O_2^{\cdot-}$ (0-200 μM).
Figure 5:
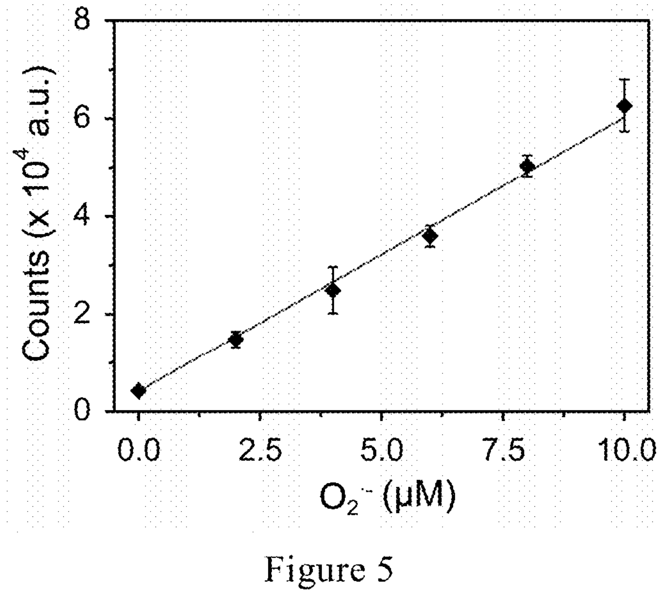
FIG. 5 shows the linear relationship between fluorescence intensity of hCy-Tf-CA (10 μM) at 730 nm and $O_2^{\cdot-}$ concentration (0-100 μM).

Under the same experimental conditions, 10 μL of probe stock solution (1 mM) was added to 1 mL of ethanol-phosphate buffer solution, the $O_2^{\cdot-}$ titration experiment was then carried out. The fluorescence intensity at 730 nm were tested 10 minutes later. FIG. 4 shows the fluorescence signal changes at 730 nm after hCy-Tf-CA (10 μM) reacted with gradient concentrations of $O_2^{\cdot-}$ (0, 20, 40, 60, 80, 100, 150, 200 μM) for 10 min. With the increase of $O_2^{\cdot-}$, the fluorescent signal of hCy-Tf-CA gradually increased. Meanwhile, the fluorescence intensity gradually increased at 740 nm and reached a plateau at 100 μM $O_2^{\cdot-}$, with a linear increase in the range of $O_2^{\cdot-}$ concentration from 0 to 100 μM. (FIGS. 4 and 5). The results show that hCy-Tf-CA can sensitively detect different concentrations of $O_2^{\cdot-}$ by fluorescence signal.

Embodiment 6

Figure 6:
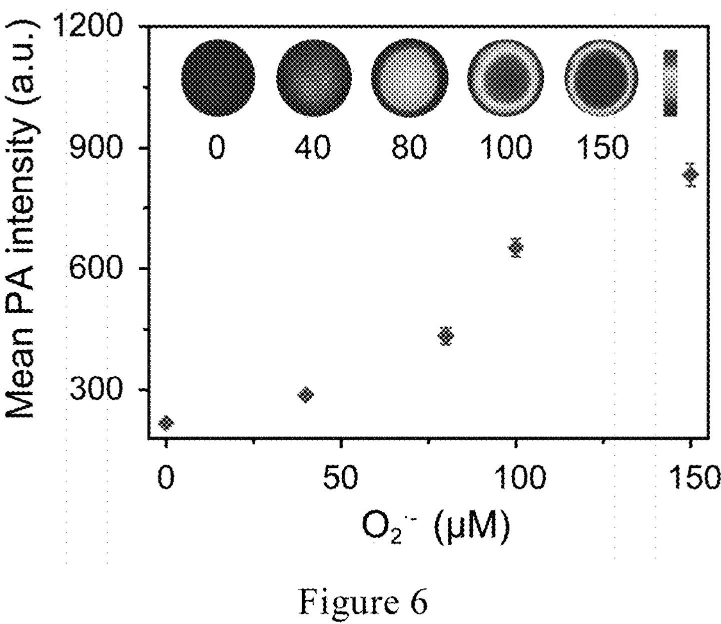
FIG. 6 shows photoacoustic intensity of hCy-Tf-CA (10 μM) at 710 nm after 10 min incubation with different concentration $O_2^{\cdot-}$ (0-100 μM).

Photoacoustic Response of hCy-Tf-CA to Different Concentration of $O_2^{\cdot-}$ Under the same experimental conditions, 10 μL of probe stock solution (1 mM) was added to 1 mL of ethanol-phosphate buffer solution, the $O_2^{\cdot-}$ titration experiment then was carried out and the photoacoustic intensity at 710 nm were tested 10 minutes later. FIG. 6 shows that the photoacoustic signal changes at 710 nm significantly increased after hCy-Tf-CA (10 μM) reacts with gradient concentrations of $O_2^{\cdot-}$ (0, 20, 40, 60, 80, 100, μM). Meanwhile, the photoacoustic images of hCy-Tf-CA recorded by a photoacoustic imaging system ($\lambda_{ex}$=710 nm) show that the photoacoustic signals were gradually increased with increasing $O_2^{\cdot-}$ concentration, proving that hCy-Tf-CA can be used to determinate $O_2^{\cdot-}$ concentrations by changes in PA signal.

Embodiment 7

Selective Response of hCy-Tf-CA to $O_2^{\cdot-}$

Figure 7:
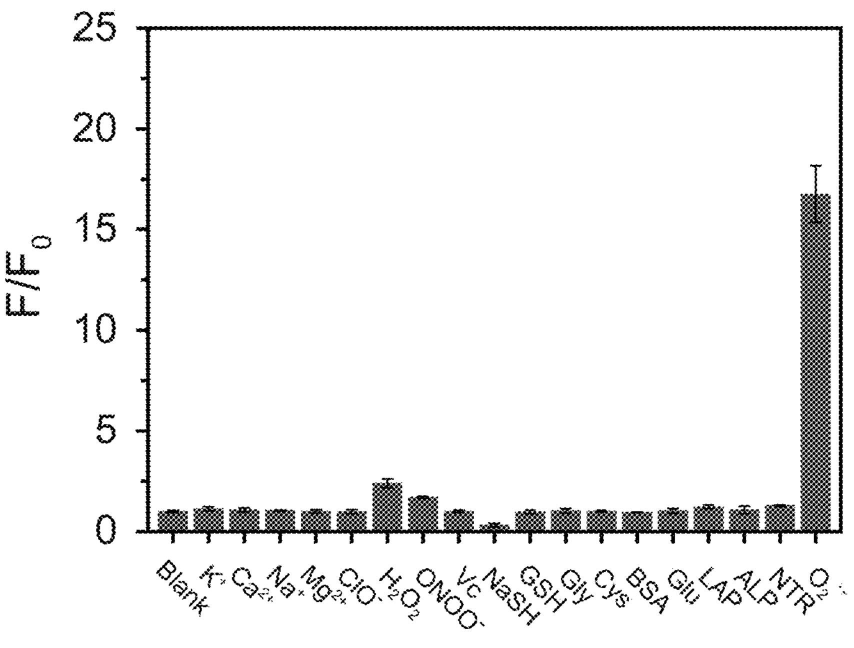
FIG. 7 shows fluorescence response of hCy-Tf-CA (10 μM) at 730 nm to different potential interfering molecules.

The specificity of hCy-Tf-CA was determined against various potential interferents ($Na^+$, $K^+$, $Ca^{2+}$, $Mg^{2+}$, $Zn^{2+}$, $Cu^{2+}$, $HS^-$, HClO, $H_2O_2$, ·OH, $ONOO^-$, glucose, glutathione, cysteine, vitamin C, nitroreductase, alkaline phosphatase, β-galactosidase and leucine aminopeptidase). Under the same experimental conditions, 10 μL of probe stock solution (1 mM) was added to 1 mL of ethanol-phosphate buffer solution. Then stock solutions of various potential interferents were respectively added to above solution, then the fluorescence intensity at 730 nm was tested. The probe hCy-Tf-CA barely respond to various potential interferents (analytes: 100 μM, enzyme: 0.1 U·mL$^{-1}$), but show significant response to $O_2^{\cdot-}$ with rapidly increased fluorescence (FIG. 7). Therefore, these potential interferents barely effect on the selective response to $O_2^{\cdot-}$, implying that the probe hCy-Tf-CA prepared by the invention has good selectivity.

In summary, the liver-targeted fluorescent/photoacoustic dual-modal probe hCy-Tf-CA prepared by the invention has high sensitivity when applied for $O_2^{\cdot-}$ detection in vitro, and can satisfy to selective detection of $O_2^{\cdot-}$ in dynamic and complex organism.

Embodiment 8

Biocompatibility Study

Inspired by the excellent responsiveness of the probe hCy-Tf-CA to $O_2^{\cdot-}$, its biocompatibility and potential for further applications in living cells were assessed. HepG2 cells were plated in a 96-well plates at $6\times10^5$ cells/well and incubated overnight in the cell incubator. Then the cells were washed with culture medium and incubated with various concentrations of hCy-Tf-CA (1, 2, 4, 8, 10 μM) at 37° C. for 24 h. After removing the above solution, CCK-8 reagent diluted with culture medium was added to each well and incubated at 37° C. for 60 min. Finally, the absorbance was finally measured at 450 nm by a microplate reader. Cell viability was calculated using the following formula:

$$\text{Calculation of cell viability: Cell viability (\%)}=(A_{experimental\ group}-A_{blank\ group})/(A_{control\ group}-A_{blank\ group})\times100\%.$$

Figure 8:
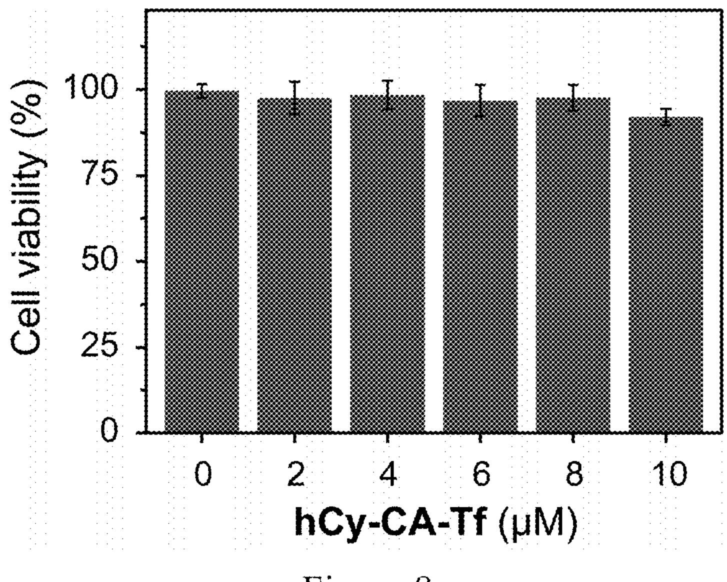
FIG. 8 shows the cytotoxicity of different concentrations of hCy-Tf-CA to HepG2 cells within 24 hours.
Figure 9:
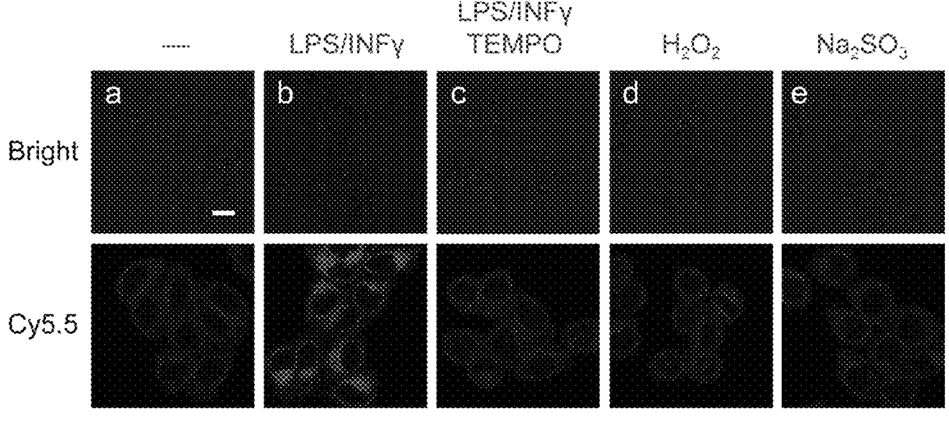
FIG. 9 shows in vitro fluorescence imaging in HepG2 cells with hCy-Tf-CA (10 μM).

Standard CCK-8 assay showed that HepG2 cells were still more than 90% viable after 24 h exposure to 10 μM hCy-Tf-CA, which proved that the cytotoxicity of hCy-Tf-CA was negligible (FIG. 8). Therefore, the biosafe hCy-Tf-CA can be used to the further experiment in living cells.

Embodiment 9

Fluorescence Imaging of Endogenous $O_2^{\cdot-}$ in HepG2 Cells

To evaluate the capacity of hCy-Tf-CA to image $O_2^{\cdot-}$ fluctuation in living cells, HepG2 cells were plated in a glass-bottom dish for 24 h to 80% density before the experiment. Cell fluorescence imaging of hCy-Tf-CA was divided into five groups. In the first group, hCy-Tf-CA (10 μM) was incubated with cells for 30 min. In the second group, cells were pretreated with lipopolysaccharide (LPS, 1 μg/mL) and interferon-gamma (IFN-γ, 50 ng/mL) for 12 h, then washed twice with PBS buffer before incubating with hCy-Tf-CA (10 μM) for 30 min. In the third group, cells were pretreated with LPS (1 μg/mL), IFN-γ (50 ng/mL) and 2,2,6,6-tetramethylpiperidine-N-oxyl (TEMPO, 300 μM) for 12 h, then washed twice with PBS buffer before incubating with hCy-Tf-CA (10 μM) for 30 min. In the fourth and fifth groups, cells were pretreated with $H_2O_2$ or $Na_2SO_3$ (100 μM) for 30 min, then washed twice with PBS buffer before incubating with hCy-Tf-CA (10 μM) for 30 min. The cells were washed 3 times with PBS buffer before cell imaging. Fluorescence images of the cells were captured by a Nikon AX R microscope with DAPI channel ($\lambda_{ex}$=404 nm, $\lambda_{em}$=425-475 nm) and Cy5.5 channel ($\lambda_{ex}$=639 nm, $\lambda_{em}$=663-738).

Figure 10:
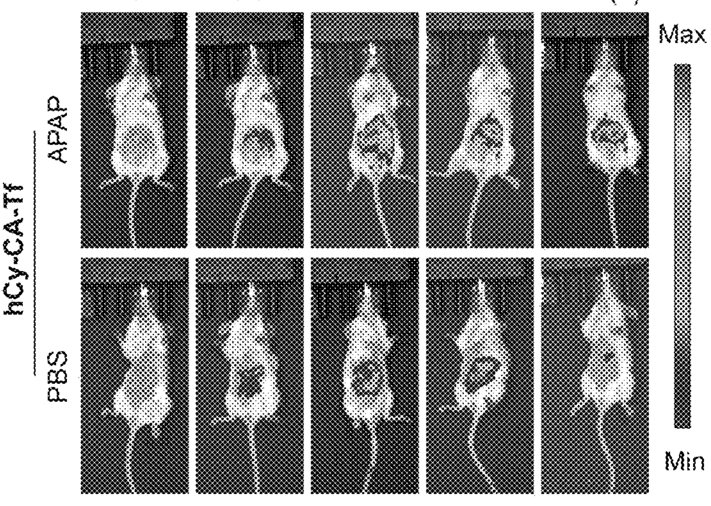
FIG. 10 shows in vivo fluorescence imaging of mouse model of drug-induced hepatic inflammation.

As shown in FIG. 10, HepG2 cells incubated with hCy-Tf-CA showed weak fluorescence, indicating a relatively low $O_2^{\cdot-}$ level under normal conditions. After incubation with LPS/IFN-γ for 12 h, the fluorescence intensity was significantly increased. At the same time, intracellular fluorescence was largely suppressed in the presence of TEMPO (2,2,6,6-tetramethylpiperidine-N-oxyl, a scavenger of $O_2^-$), implying the specificity of hCy-Tf-CA in monitoring cellular $O_2^-$ fluctuations. In addition, $H_2O_2$ was selected as the representative ROS and $SO_3^{2-}$ as the nucleophile to further evaluate its anti-interference. In $H_2O_2$-treated or $SO_3^{2-}$-treated cells, the fluorescence fluctuations were negligible. In short, these results proved the capacity of hCy-Tf-CA to selectively detect $O_2^-$ in living cells.

Embodiment 10

Precise Detection of Drug-Induced Hepatic Inflammation by Fluorescence/Photoacoustic Dual-Modal Imaging In order to visually detect hepatic $O_2^-$ concentration and drug-induced hepatic inflammation by fluorescence/photoacoustic dual-modal imaging, Balb/c female mice were intraperitoneally injected with overdose of APAP (300 mg/Kg) to cause drug-induced hepatic inflammation, and PBS injected mice served as the control group. The probe hCy-Tf-CA (50 μM, 100 μL) were administrated intravenously for in vivo fluorescence/photoacoustic dual-modal imaging. Images at predetermined time points were recorded on IVIS imaging system (Perkin Elmer, $\lambda_{ex}$=675 nm, $\lambda_{em}$=760 nm) and InVision 256-TF imaging system (iThera Medical, $\lambda_{ex}$=710 nm).

Figure 11:
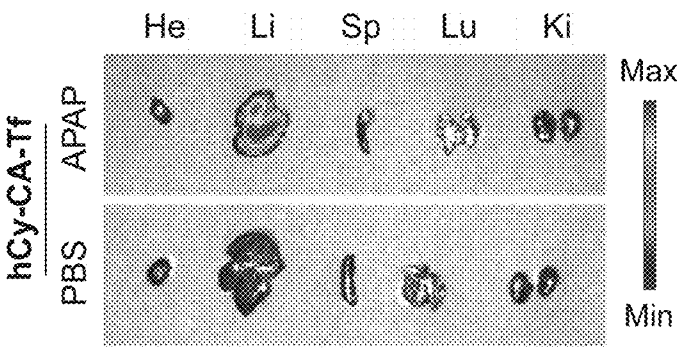
FIG. 11 shows ex vivo fluorescence imaging of mouse model of drug-induced hepatic inflammation.
Figure 12:
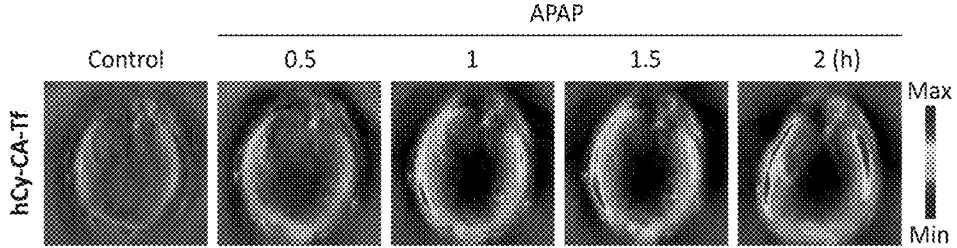
FIG. 12 shows in vivo photoacoustic imaging of mouse model of drug-induced hepatic inflammation.

As shown in FIG. 10, images at predetermined time points (0, 30, 60, 90, and 120 min) after injection of hCy-Tf-CA were recorded. The fluorescence signal in abdomen gradually increased in hCy-Tf-CA-treated groups over time. At 2 h post-injection, the fluorescence signal intensity of APAP-treated mice was significantly higher than that of control mice, indicating that the probe molecules enter the liver through the vein, where they were reconverted to an activated state by pathological $O_2^-$. The mice were sacrificed 2 h after intravenous administration for ex vivo imaging. The fluorescence signal was mainly located in the liver and was negligible in other organs (heart, spleen, lung and kidney), and the hepatic fluorescence signal of APAP-treated mice was obviously higher than that of health mice (FIG. 11). The photoacoustic signal in mice liver gradually increased in hCy-Tf-CA-treated mice over time (FIG. 12). The PA signal from uncaged hCy-CA could indicate the hepatic $O_2^-$ concentration in cross-sectional images, also photoacoustic signal in the liver of APAP-treated mice was significantly higher than that of healthy mice. The introduction of cholic acid effectively promotes probe accumulation in the liver, and once exposed to pathologic level $O_2^-$ of hepatopathy, the probes were sensitively reconverted into activated hCy-CA. Therefore, the degree of hepatic inflammation can final be detected by significant fluorescence/photoacoustic signal in the liver region. Therefore, the probe hCy-Tf-CA can be used as an effective fluorescent/photoacoustic dual-modal probe to visually detect drug-induced hepatic inflammation.

Embodiment 10

Precise Detection of Autoimmune Hepatitis by Fluorescence/Photoacoustic Dual-Modal Imaging In order to visually detect autoimmune hepatitis by fluorescence/photoacoustic dual-modal imaging, Balb/c female mice were intravenously injected with a single dose Con A (20 mg/Kg, dissolved in 100 μL PBS) for 2 h to induce early autoimmune hepatitis, and the remaining mice were treated with PBS solution as controls. hCy-Tf-CA was then intravenously injected into mice for in vivo imaging, and representative NIRF/PA dual-modal images of different treated mice were recorded at chosen times. Images at predetermined time points were recorded on IVIS imaging system (Perkin Elmer, $\lambda_{ex}$=675 nm, $\lambda_{em}$=760 nm) and InVision 256-TF imaging system (iThera Medical, $\lambda_{ex}$=710 nm).

Figure 13:
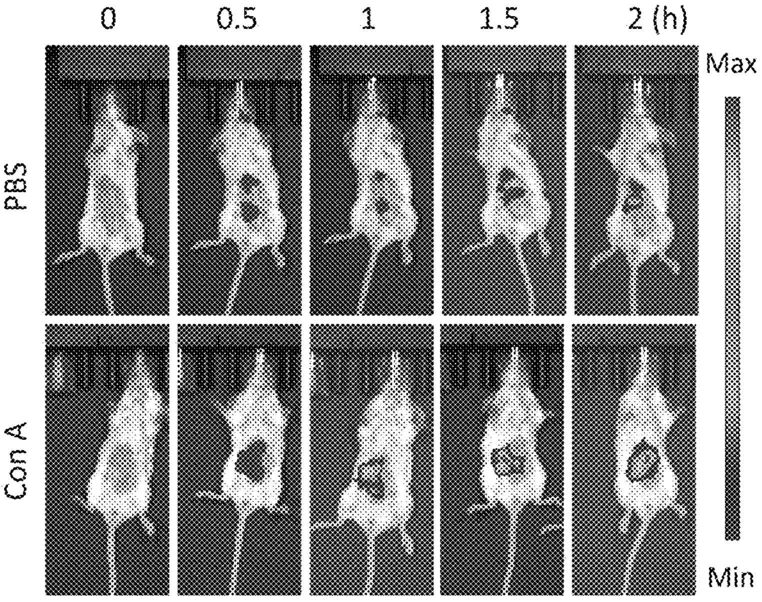
FIG. 13 shows in vivo fluorescence imaging of mouse model of autoimmune hepatitis.
Figure 14:
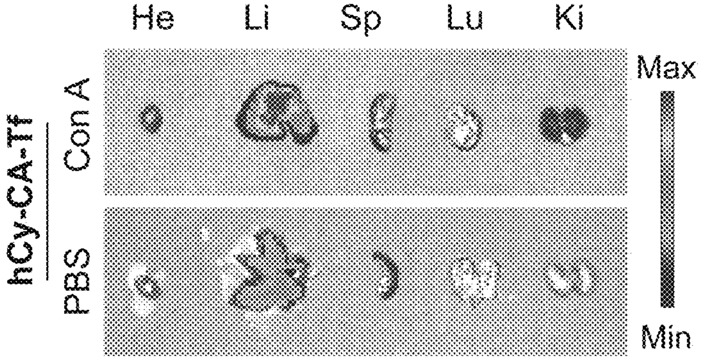
FIG. 14 shows ex vivo fluorescence imaging of mouse model of autoimmune hepatitis.
Figure 15:
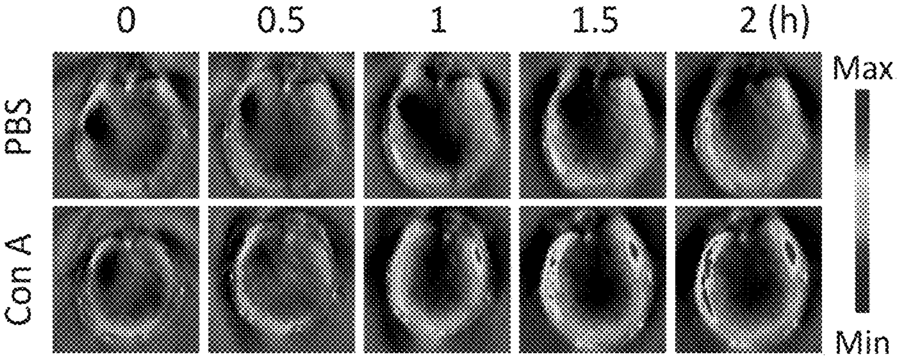
FIG. 15 shows in vivo photoacoustic imaging of mouse model of autoimmune hepatitis.
Figure 16:
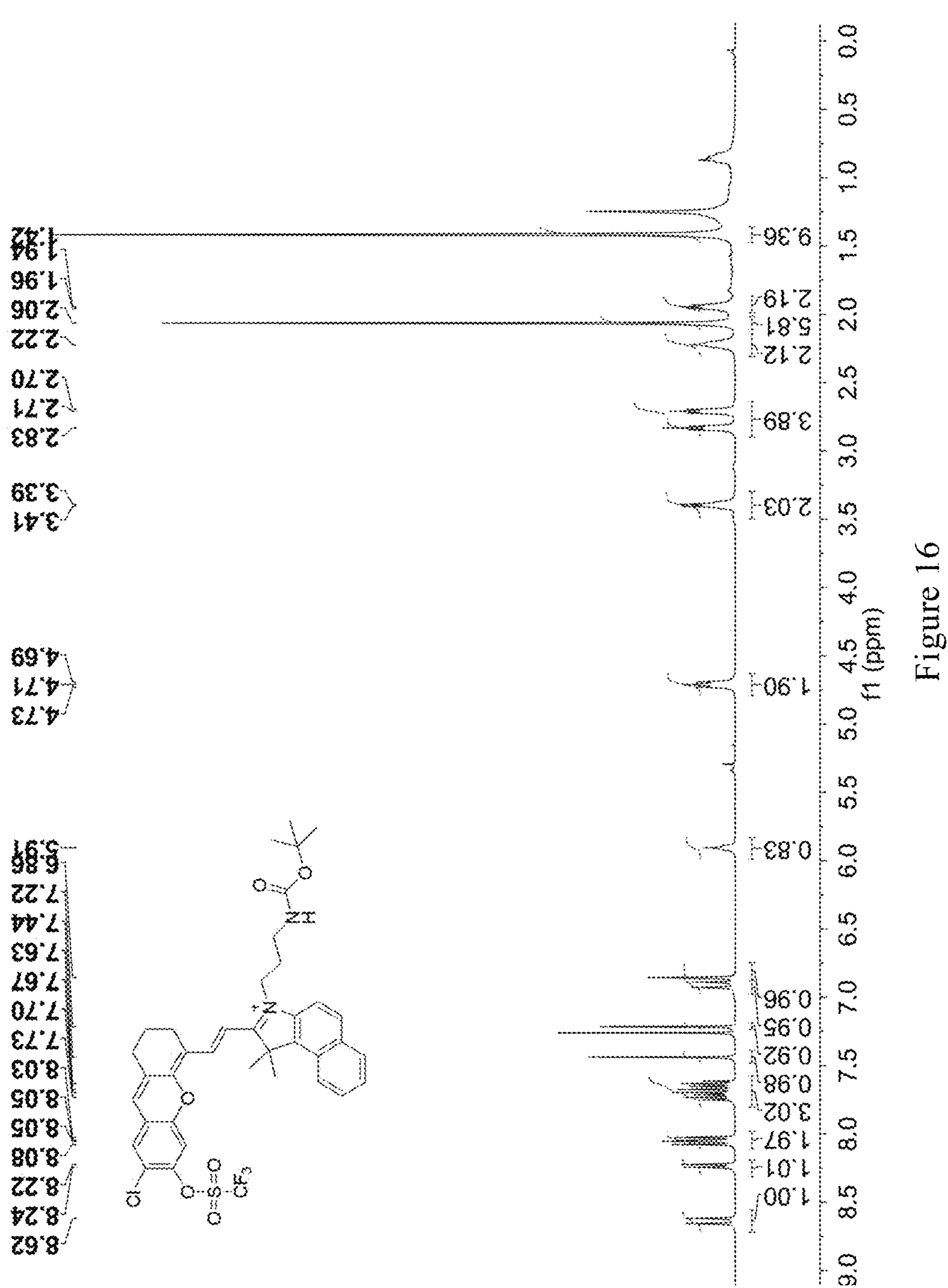
FIG. 16 shows $^{1}H$ NMR spectrum of hCy-Tf-NHBoc.
Figure 17:
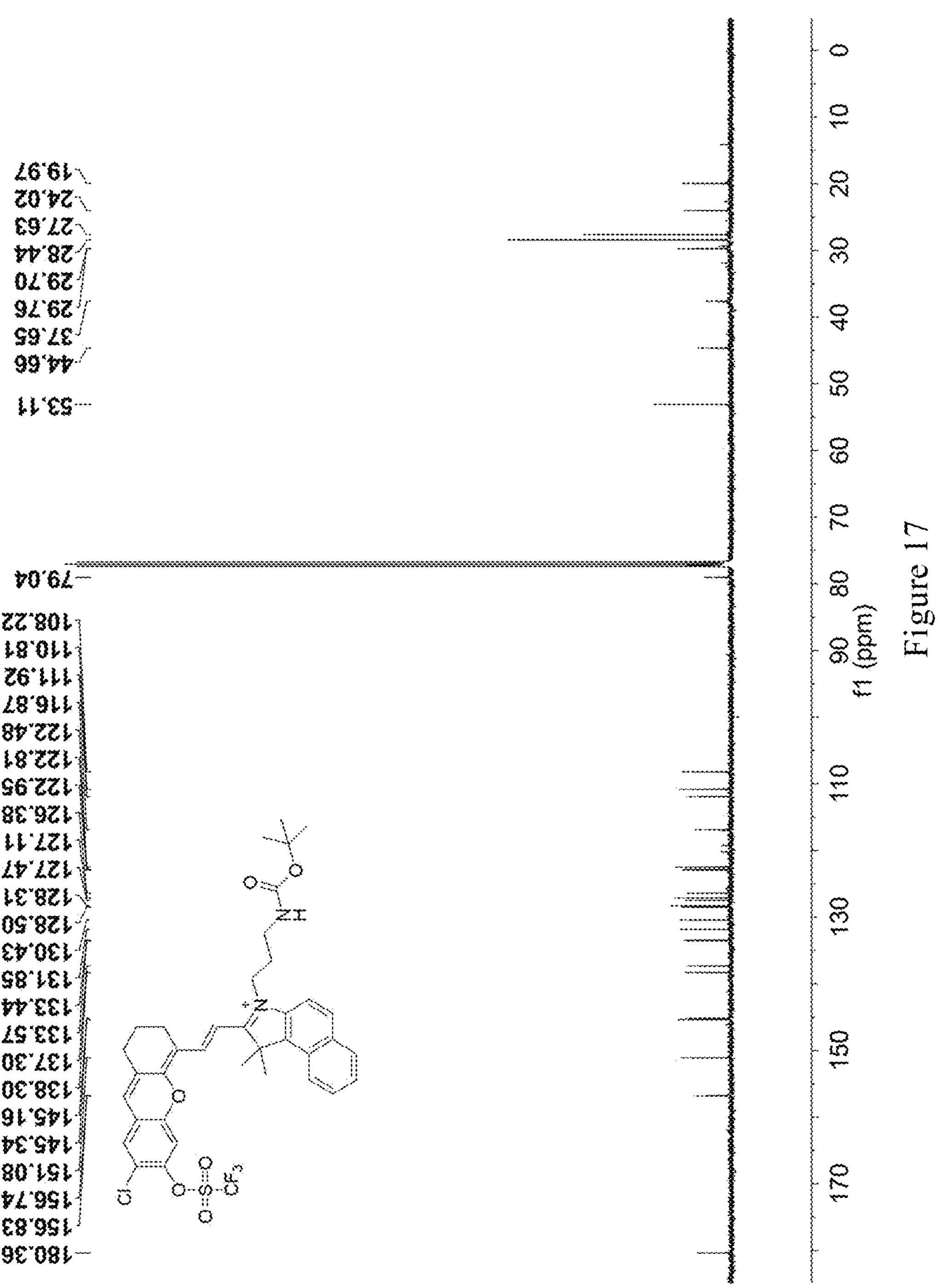
FIG. 17 shows $^{13}C$ NMR spectrum of hCy-Tf-NHBoc.
Figure 18:
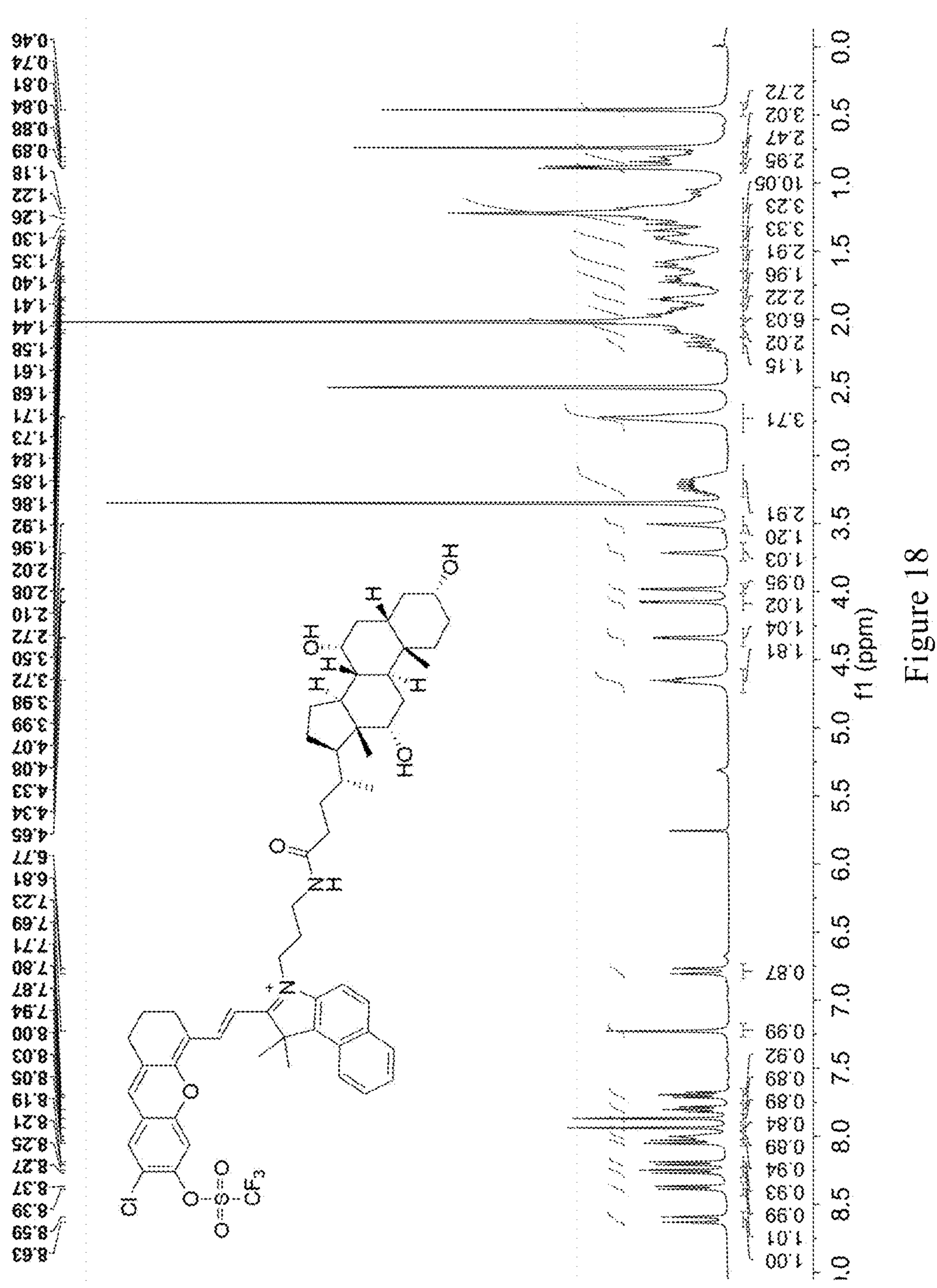
FIG. 18 shows $^{1}H$ NMR spectrum of hCy-Tf-CA.
Figure 19:
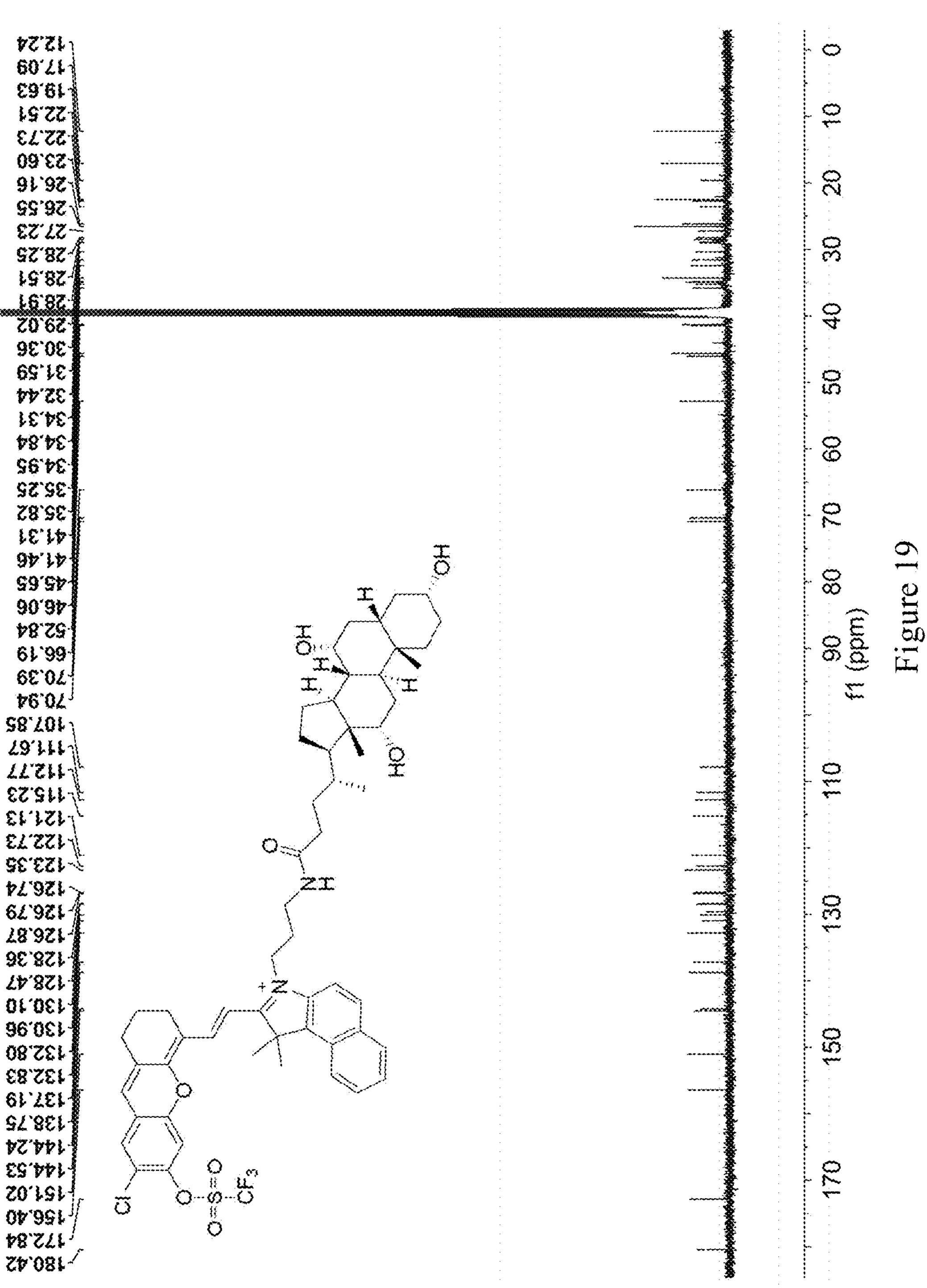
FIG. 19 shows $^{13}C$ NMR spectrum of hCy-Tf-CA.

As shown in FIG. 13, fluorescence images were recorded at predetermined time points after injection of hCy-Tf-CA. The fluorescence signal intensity in the liver region of Con A-treated mice was gradually enhanced, whereas the abdominal fluorescence signal in healthy mice was weak. Fluorescence signals in both groups were mainly located in the liver, and the signals in Con A-treated mice were apparently brighter than those in control mice (FIG. 14). Photoacoustic images of transverse sections of the liver region showed a similar trend (FIG. 15). After injection of hCy-Tf-CA, the hepatic photoacoustic signal of Con A-treated mice increased faster than that of control mice. The photoacoustic signal in the liver of Con A-treated mice was obviously higher than that of healthy mice at 2 h, which illustrates the capability of hCy-Tf-CA to detect autoimmune hepatitis in vivo through the difference in dual-modal signal.

What is claimed is:

1. A liver-targeted fluorescent/photoacoustic dual-modal probe hCy-Tf-CA for real-time imaging of in situ hepatic inflammation, having the following chemical structure:

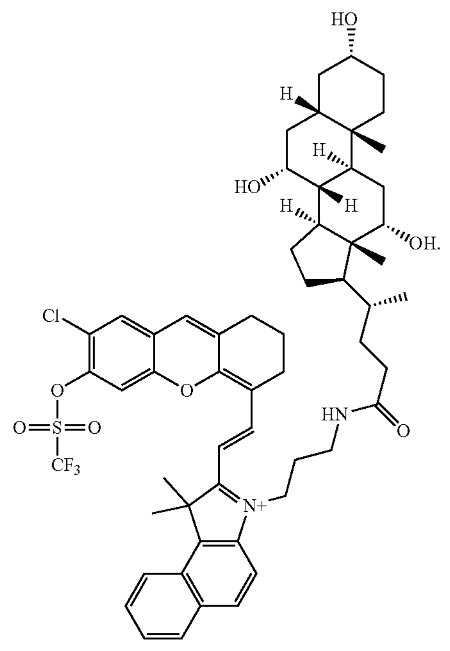

2. A method for preparing a liver-targeted fluorescent/photoacoustic bimodal probe, wherein:

Trifluoromethanesulfonic anhydride is dropwise added to a mixture of hCy-NHBoc and triethylamine in anhydrous dichloromethane in an ice bath under nitrogen atmosphere; after stirring for 5 minutes, it is quenched by ice water, an organic layer is separated and directly purified by column chromatography to afford intermediate hCy-Tf-NHBoc as a purple solid; subsequently, the intermediate hCy-Tf-NHBoc is added anhydrous dichloromethane containing 25% trifluoroacetic acid; after stirring for 5 minutes, the reaction solution is evaporated under reduced pressure and the resulting residue is washed with diethyl ether to afford crude intermediate hCy-Tf-$NH_2$; then hCy-Tf-$NH_2$, cholic acid, o-Benzotriazol-1-yl-N,N,N',N'-tetramethyluronium hexafluorophosphate, 1-Hydroxybenzotriazole and N,N-Diisopropylethylamine are dissolved in N,N-Dimethylformamide; after the reaction is complete, the solvent is removed by excess petroleum ether, and the resulting residue is purified by column chromatography to afford the liver-targeted fluorescence/photoacoustic dual-modal probe hCy-Tf-CA as a purple solid,
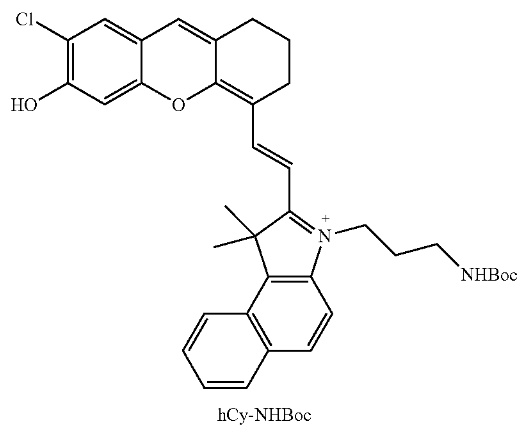
hCy-NHBoc
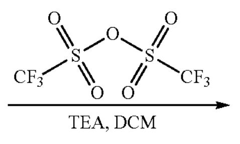
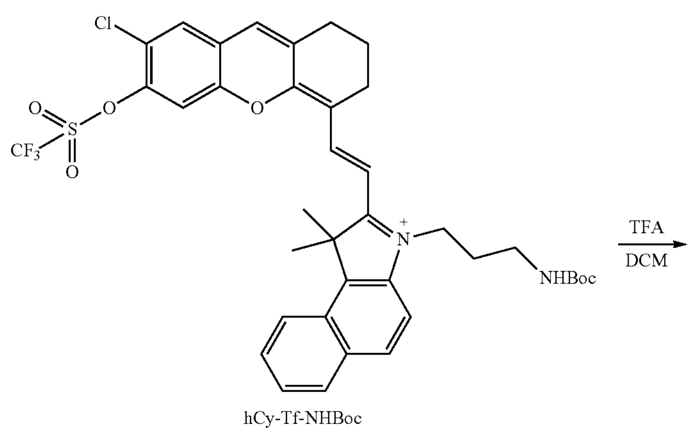
hCy-Tf-NHBoc
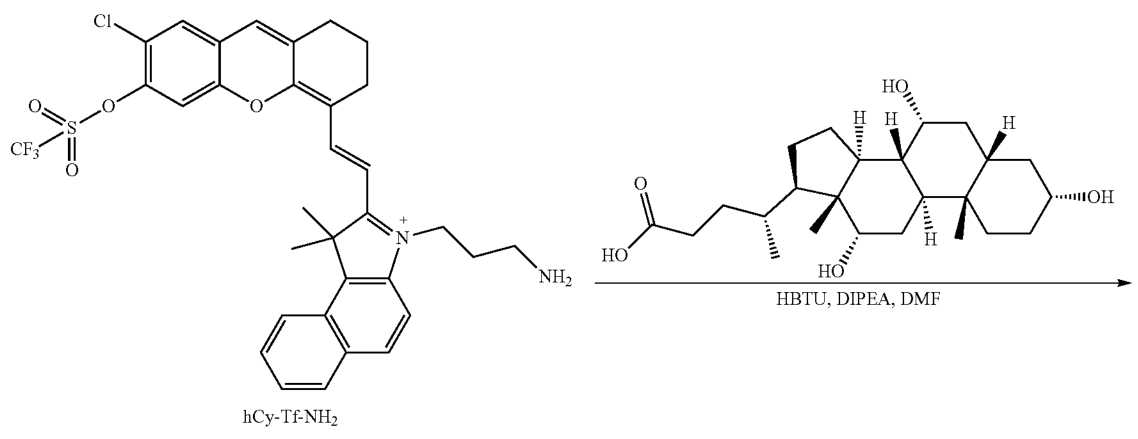
hCy-Tf-NH2
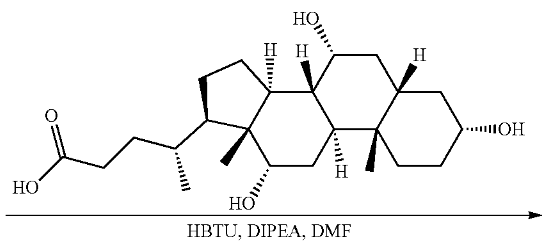

-continued

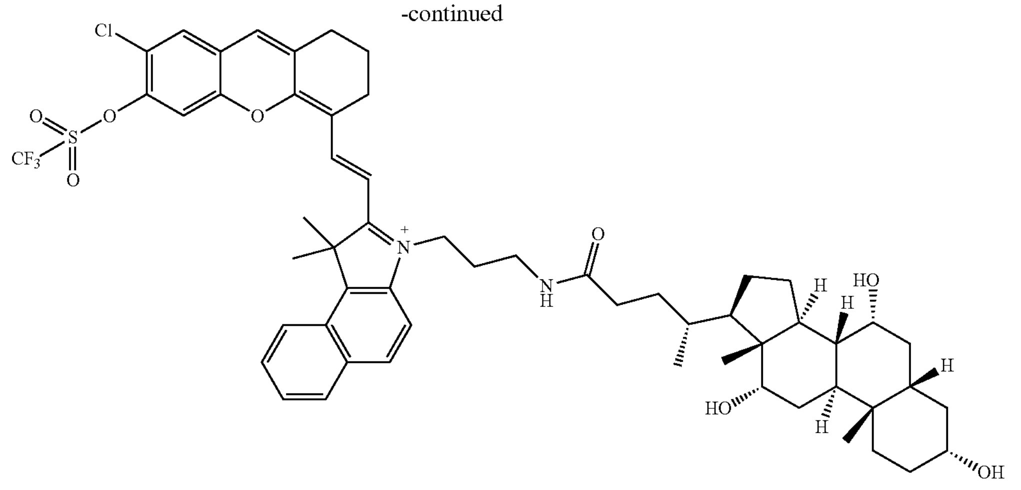

hCy-Tf-CA the molar ratio of hCy-NHBoc, trifluoromethanesulfonic anhydride and triethylamine is 1:1.2:1.2;

the volume ratio of methanol to dichloromethane is 1:50 in the first silica gel column chromatography;

the molar ratio of hCy-Tf-NHBoc to trifluoroacetic acid is 1:536;

the molar ratio of hCy-Tf-$NH_2$, cholic acid, o-Benzotriazol-1-yl-N,N,N',N'-tetramethyluronium hexafluorophosphate, 1-Hydroxy benzotriazole and N,N-Diisopropylethylamine is 1:1.2:1.2:1.2:2;

the volume ratio of methanol to dichloromethane is 1:10 in the second silica gel column chromatography.

* * * * *